(12) United States Patent
Kirchhofer et al.

(10) Patent No.: US 7,727,202 B2
(45) Date of Patent: Jun. 1, 2010

(54) MULTI-COMPONENT PISTON STOPPER

(75) Inventors: Fritz Kirchhofer, Sumiswald (CH); Michel Hirsiger, Hinterkapplen (CH); Frank Schiffmann, Burgdorf (CH); Hanspeter Stoller, Bern (CH)

(73) Assignee: TecPharma Licensing AG, Burgdorf (CH)

(*) Notice: Subject to any disclaimer, the term of this patent is extended or adjusted under 35 U.S.C. 154(b) by 0 days.

(21) Appl. No.: 10/218,680

(22) Filed: Aug. 14, 2002

(65) Prior Publication Data

US 2003/0153876 A1    Aug. 14, 2003

Related U.S. Application Data

(63) Continuation of application No. PCT/CH01/00096, filed on Feb. 13, 2001.

(30) Foreign Application Priority Data

Feb. 15, 2000   (DE) ................ 100 06 560

(51) Int. Cl.
*A61M 5/315*  (2006.01)

(52) U.S. Cl. .............. 604/222; 604/218; 604/187

(58) Field of Classification Search .......... 604/218, 604/219, 220, 221, 222, 223, 224, 225, 226, 604/228, 230, 187
See application file for complete search history.

(56) References Cited

U.S. PATENT DOCUMENTS

| | | | | |
|---|---|---|---|---|
| 2,895,773 A | * | 7/1959 | McConnaughey | 92/245 |
| 3,059,639 A | * | 10/1962 | Blackman et. al. | 604/222 |
| 3,747,479 A | * | 7/1973 | Nightingale et al. | 92/203 |
| 3,993,061 A | * | 11/1976 | O'Leary | 604/152 |
| 4,030,496 A | * | 6/1977 | Stait et al. | 604/222 |
| 4,363,329 A | * | 12/1982 | Raitto | 600/578 |
| 4,498,904 A | * | 2/1985 | Turner et al. | 604/211 |
| 4,657,028 A | * | 4/1987 | Rich et al. | 600/578 |
| 4,852,768 A | * | 8/1989 | Bartsch | 222/46 |
| 4,946,455 A | * | 8/1990 | Rosen | 604/403 |
| 5,226,897 A | | 7/1993 | Nevens et al. | |
| 5,397,313 A | | 3/1995 | Gross | |
| 5,697,917 A | * | 12/1997 | Sadowski et al. | 604/218 |
| 5,735,825 A | * | 4/1998 | Stevens et al. | 604/218 |
| 5,902,276 A | | 5/1999 | Namey, Jr. | |
| 5,909,836 A | * | 6/1999 | Shkolnikov et al. | 227/8 |
| 5,997,511 A | * | 12/1999 | Curie et al. | 604/195 |
| 6,004,300 A | * | 12/1999 | Butcher et al. | 604/222 |
| 6,280,418 B1 | * | 8/2001 | Reinhard et al. | 604/187 |
| 6,764,461 B2 | * | 7/2004 | Mickley et al. | 604/15 |

FOREIGN PATENT DOCUMENTS

| | | |
|---|---|---|
| CH | 268694 | 5/1950 |
| EP | 0925789 A1 | 6/1999 |
| EP | 1099449 A1 | 5/2001 |
| FR | 1006965 | 5/1952 |

\* cited by examiner

*Primary Examiner*—Nicholas D Lucchesi
*Assistant Examiner*—Laura A Bouchelle
(74) *Attorney, Agent, or Firm*—Dorsey & Whitney LLP; David E. Bruhn

(57) ABSTRACT

A piston stopper for a medicine injector, wherein the stopper has a stopper body with a mesh section and at least one sealing element positioned at least partly around the circumference of the stopper body, wherein at least one of the sealing element and mesh section is connected to the stopper body in a material bond. A method for manufacturing such a piston stopper is encompassed.

11 Claims, 5 Drawing Sheets

MULTI-COMPONENT PISTON STOPPER

PRIORITY CLAIM

This application is a Continuation of International Application No. PCT/CH01/00096, filed on Feb. 13, 2001, which claims priority to German Application No. DE 100 06 560.0, filed on Feb. 12, 2000, both of these applications are incorporated herein by reference.

BACKGROUND

The invention relates to a piston stopper for a medicine injector and to a method for manufacturing a piston stopper.

Medicine injectors conventionally comprise a cylindrical receptacle for a liquid medicine which is injected out through a cannula by means of a piston. These pistons typically have a shaft and a piston stopper which seals the cylinder off against its inner wall. To this end, pistons are conventionally used which are provided with at least one sealing ring positioned in a circumferential groove. In known embodiments, the piston stopper consists of a relatively hard material and a sealing ring or sealing rings, which consist of a softer material for a better seal, are inserted into the circumferential grooves elastically like rubber. Thus, they are held in the grooves only by their own elasticity.

In the above, conventional embodiments, the sealing rings have to be installed in a separate step, which is therefore time-consuming. Also, the sealing rings' hold in the circumferential grooves is heavily dependent on the spring elasticity of the sealing rings, such that poorly produced sealing rings, or rings manufactured from a material which is already quite old or otherwise flawed, easily slip out of the grooves. Because the sealing rings are simply tensioned into the grooves, the danger always exists that they may leave the groove in which they are received or be badly twisted in their hold during use, giving rise to major leakage problems.

Attempt have been made to solve this problem. One attempt involves manufacturing piston stoppers from a soft solid-rubber material as complete components, wherein the sealing rings are merely formed as protruding circumferential attachments of the stopper material. Even this solution, however, involves problems, specifically when there is a high counter pressure from the liquid to be expelled. Such a high counter pressure can, for example, arise when a cannula is deformed or kinked. Because of the totally soft material of the stopper, the latter gives in such cases and the piston travels further forward in the outlet direction, wherein the liquid between the piston and the cylindrical inner wall is pressed backwards. In particular, when using injectors which are outwardly sealed, for example, so-called "pens," there is the possibility that a patient would not even notice this process and believe that he or she has injected the medicine, when in fact it has flowed past the piston into the rear inner space of the cylinder.

Furthermore, piston stoppers in accordance with the prior art usually simply comprise threaded sections moulded into the stopper body, which do not establish an optimal connection with a plunger.

SUMMARY

It is an object of the present invention to provide a piston stopper for a medicine injector and a method for its manufacture, so as to overcome the above disadvantages of the prior art. In particular, a piston stopper is to be provided which allows an optimum mesh with components connected to it. As used herein, "mesh" is intended to be synonymous with connection, bond, joint, tie, link, bind, joining and the like. Specifically, a piston stopper in accordance with the present invention should provide optimum impermeability, be easy to produce, and exhibit an optimum connection with a plunger.

In one embodiment, these objects are addressed by a piston stopper for a medicine injector which comprises a stopper body comprising a mesh section, in particular a threaded mesh section for receiving a plunger, and at least one sealing element positioned at least partly around the circumference of the stopper body, the sealing element and/or the mesh section, in particular the threaded mesh section, being connected to the stopper body in a material bond. As used herein, the term "material bond" is intended to encompass any suitable form or method of adhesion, coupling or connection brought about in any suitable manner, including, for example, by glues, heating, adhesives, fusion, welding, deformation, etc.

In one embodiment, the present invention comprises a piston stopper for a medicine injector or injection device. The piston stopper comprises a stopper body comprising a mesh section, which also may be referred to as a connection region, and at least one sealing element positioned at least partly around the circumference of the stopper body, at least one of the sealing element and mesh section being connected to the stopper body via a material bond.

In one embodiment, a piston stopper in accordance with the present invention comprises a stopper body comprising a connection region and at least one sealing element positioned at least partly around the stopper body, at least one of the sealing element and connection region being connected to the stopper body via a material bond. In some embodiments, the connection region comprises threads for receiving the threads of a threaded plunger.

In some embodiments, the sealing element in accordance with the invention is thus a separate or discretely provided sealing element, but is non-detachably connected to the stopper body by the material bond, once it is attached thereto. Thus it can advantageously no longer be twisted or escape from its positioning means, avoiding potential leakage problems associated with the prior art. Furthermore, the material bond enables the sealing element to accurately maintain the position of its sealing area, and a definite position of said sealing area can be assumed when manufacturing the piston stopper, such that effective improvements to the sealing area, for example specific shaping, can be realized. This still retains the advantage that the stopper can be manufactured from different materials, for example from a hard material for the stopper body and from a soft material for the sealing element or elements. The problems of soft stopper bodies, as described above, are accordingly avoided.

The above also applies correspondingly to the stopper body connection with a plunger. In accordance with another aspect of the invention, the mesh or connection section, in particular the threaded mesh section, for a plunger can also or solely be connected to the stopper body in or via a material bond. This creates the possibility of establishing an optimum and specifically secure and/or damped mesh or connection with the plunger by selecting for the mesh section a suitable material having a suitable, selected hardness or softness. Here, too, the material bond allows the position to be fixed reliably.

It is possible within the framework of the invention to position one, two or more sealing elements on a stopper body. The number will depend on the application in question, and the sealing elements can be positioned in circumferential recesses, for example grooves, of the stopper body, in the form of sealing rings.

Furthermore, a sealing cap comprising a circumferential sealing lip can be positioned forwards on the stopper body. Such a sealing lip is then advantageously formed as an annular protrusion extending from the cap, and projecting from the cap body obliquely forward, i.e., towards the volume of liquid to be displaced.

In one embodiment of the invention, at least one of the sealing element and the mesh section is adhered at its respective contact area to the stopper body. In other embodiments, at least one of the sealing element and mesh section, in particular a threaded mesh section, can be provided which is formed integrally at its contact area with the stopper body. As used herein, "integrally formed" is intended to mean that the materials of the sealing element and/or mesh section and the stopper body are combined to form a continuous material. This may be achieved by, for example, fusing the sealing element and/or the mesh section at their or its contact area to the stopper body. The stopper body and sealing element are preferably fused or integrally formed in a bi-component injection molding, wherein the sealing element and/or the mesh section, in particular the threaded mesh section, is injection moulded onto the stopper body at the contact area. The contact area is heated as a result, ensuring that it fuses to form a material bond.

The stopper body is preferably formed from a thermoplast, in particular a relatively hard, non-elastomeric thermoplast, preferably from propylene, and the sealing element and/or the mesh section, in particular the threaded mesh section, is preferably likewise formed of a thermoplast, in particular from a relatively soft, elastomeric thermoplast, preferably from Santopren.

In order to promote and/or simplify fusion, in some embodiments of the present invention materials having melting points not more than about 35° C. apart, in particular not more than about 20° C. to 25° C. apart, are used for the stopper body and the sealing element and/or the mesh section.

In accordance with a preferred embodiment of the piston stopper, the sealing element forms a tongue in the area of its outer sealing area, when it is formed as a sealing ring, in order to further increase the liquid seal when the liquid is injected out. It is particularly advantageous if the sealing tongue is arranged on the outer side of a concave front recess, wherein the front side is to be regarded as the side facing the liquid in the injector cylinder.

DETAILED DESCRIPTION

Figure 6:
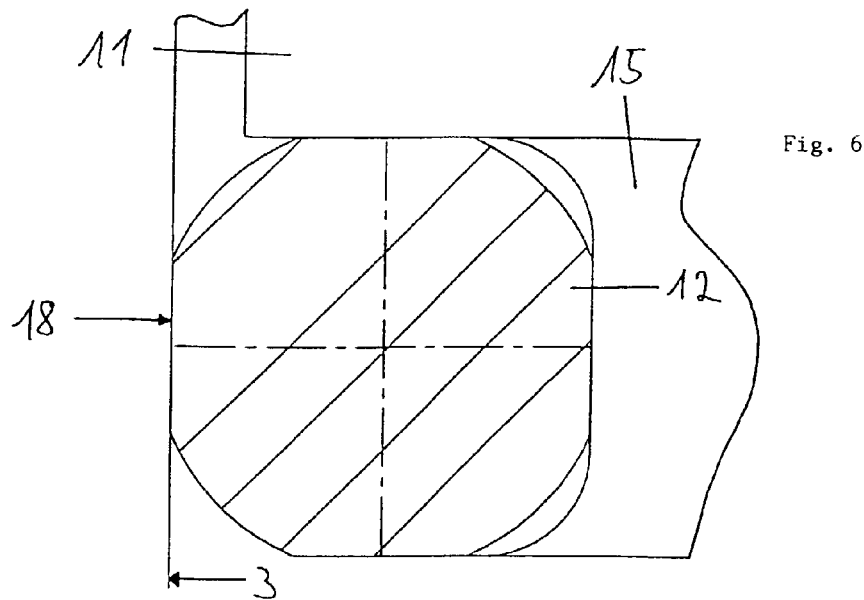
FIGS. 6 and 7 depict representations corresponding to FIGS. 1 and 2 and FIGS. 3 and 4, respectively, for a piston stopper in accordance with the prior art.
Figure 7:
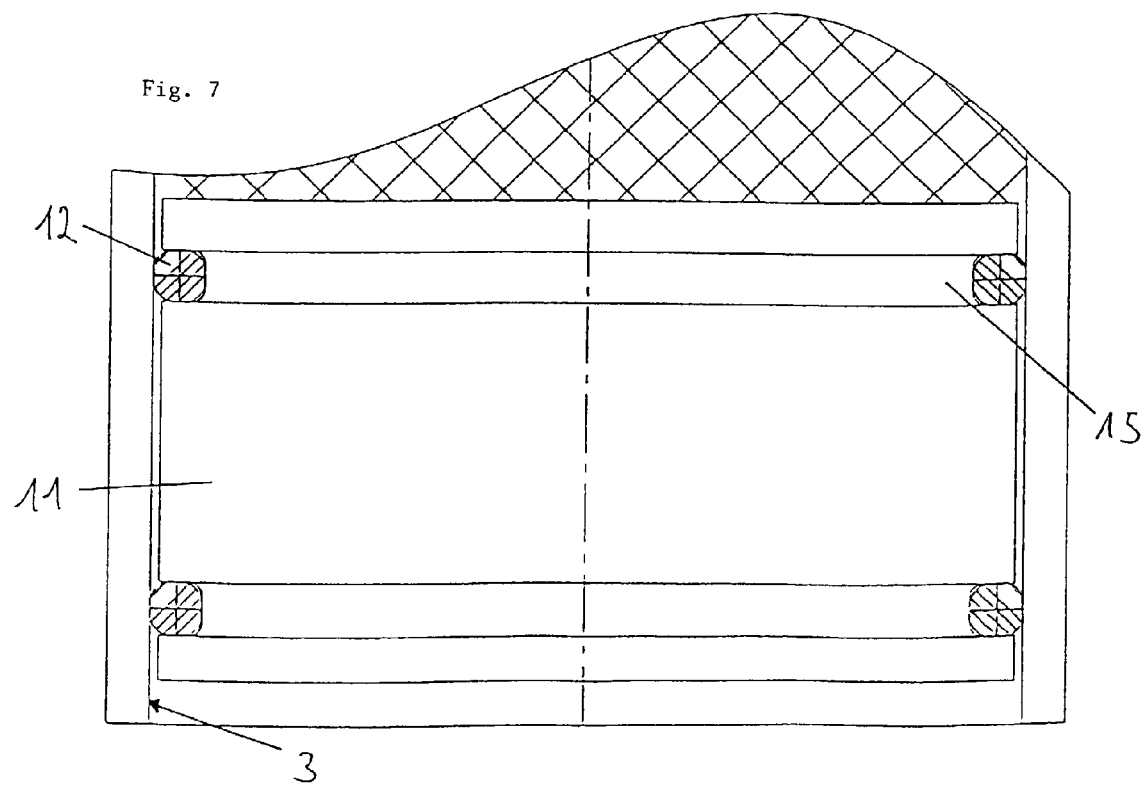

The invention improves a piston stopper comprising a relatively hard material for the stopper body and soft sealing rings. Such a conventional piston stopper, comprising a sealing ring loosely positioned in a groove, is shown in FIGS. 6 and 7. The piston stopper 11, which as shown in FIG. 7 is positioned in a glass piston, comprises the groove 15 into which the sealing ring 12 is loosely inserted. The sealing ring 12 is held in the groove 15 only by its inner tension force, however, intermediate spaces still arise in the area of the contact areas with the piston 10 and with the interior of the groove 15, as depicts in FIG. 6. The loose fitting of the ring 12 allows the ring 12 to be deformed, twisted and possibly even to escape from the groove 15, and thus leads to leakage problems. Also, if the ring is deformed, the contact area 18 at which the ring 12 contacts the inner wall 3 of the cylinder can no longer be maintained in its original form, and is, above all, not clearly defined on the ring, due to possible movement of the ring 12.

Figure 1:
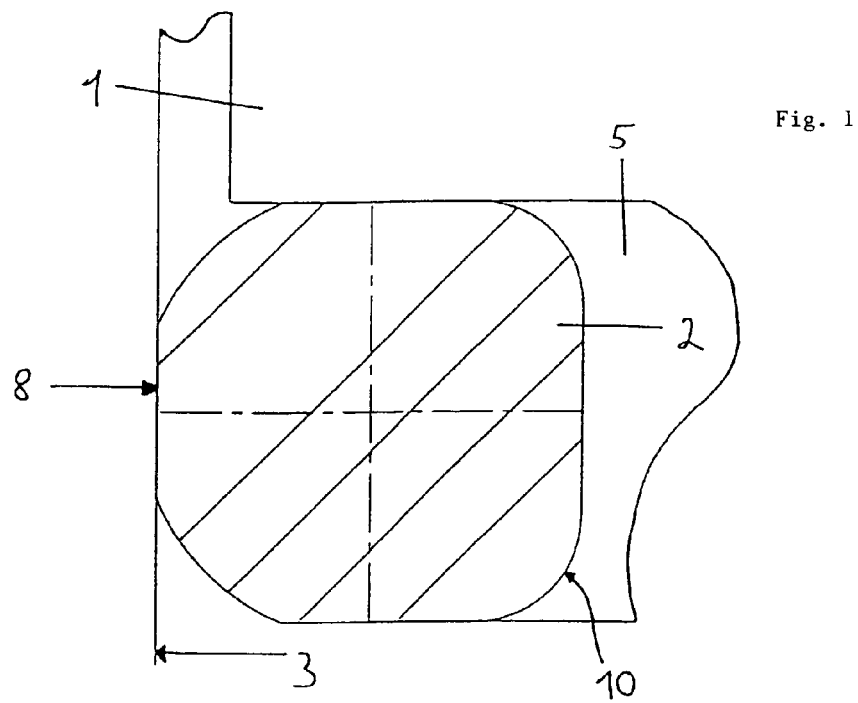
FIG. 1 depicts an area of a piston stopper comprising a sealing ring in accordance with the invention, enlarged in sections.
Figure 2:
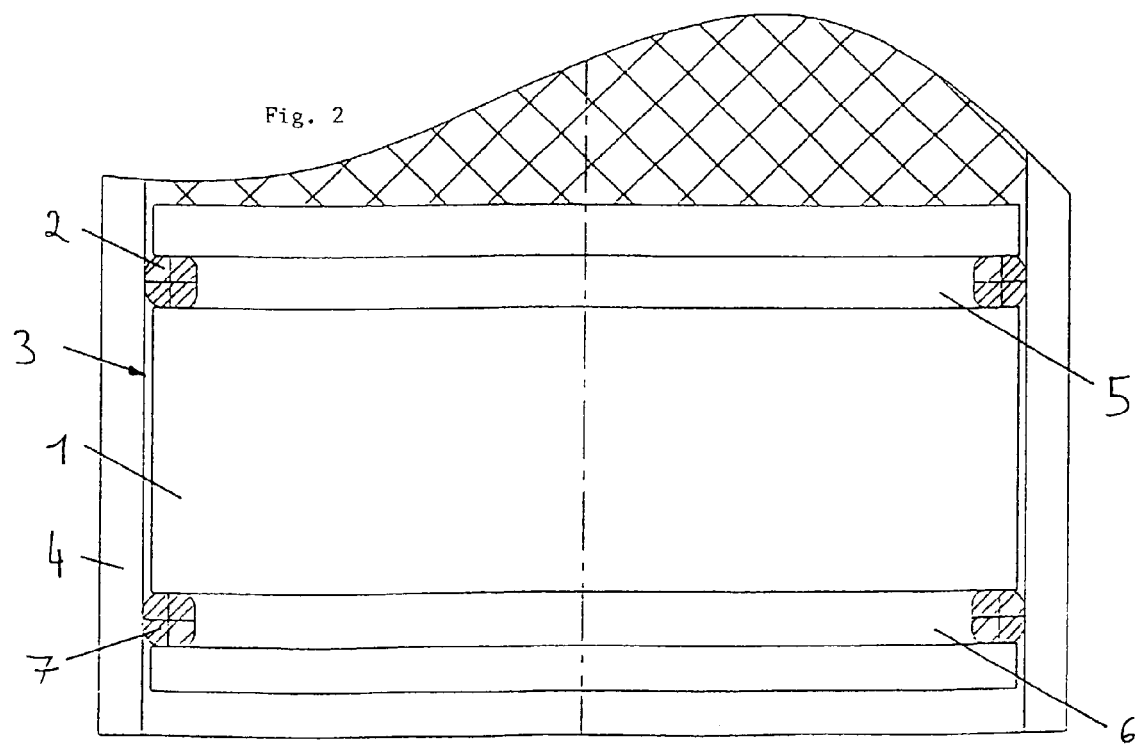
FIG. 2 depicts the piston stopper according to FIG. 1, in an overall view in an injector cylinder.

One version of an improved embodiment of a piston stopper in accordance with the invention is shown in FIGS. 1 and 2, wherein FIG. 1 shows, in an enlargement of FIG. 2, an area around a sealing ring 2.

The piston stopper in accordance with the invention consists of the stopper body 1, which comprises two circumferential grooves 5 and 6. Sealing rings 2, 7 are positioned in these circumferential grooves, in a suitable material bond with the material of the stopper body 1 and/or the grooves 5, 6. The rings 2, 7 are connected at a contact area 10 (FIG. 1) to the material of the stopper body in a non-detachable material bond, by being adhered or fused. This prevents the rings 2, 7 from being twisted or moved in the grooves 5, 6, or partly or completely leaving them. Thus, the rings remain non-deformed and positionally stabilized with respect to stopper body 1, and can therefore fulfill their sealing function substantially better than a loosely inserted ring such as is used in the piston stopper in accordance with the prior art (FIGS. 6 and 7).

In particular through this positional stability, a better seal results from the fact that the contact area 8 at which the piston contacts the inner wall 3 of the surrounding cylinder 4 is a defined and substantially unvarying area whose form will be only very slightly altered by the shifting process of the piston stopper. This circumstance also substantially guarantees the impermeability of the piston stopper.

Figure 3:
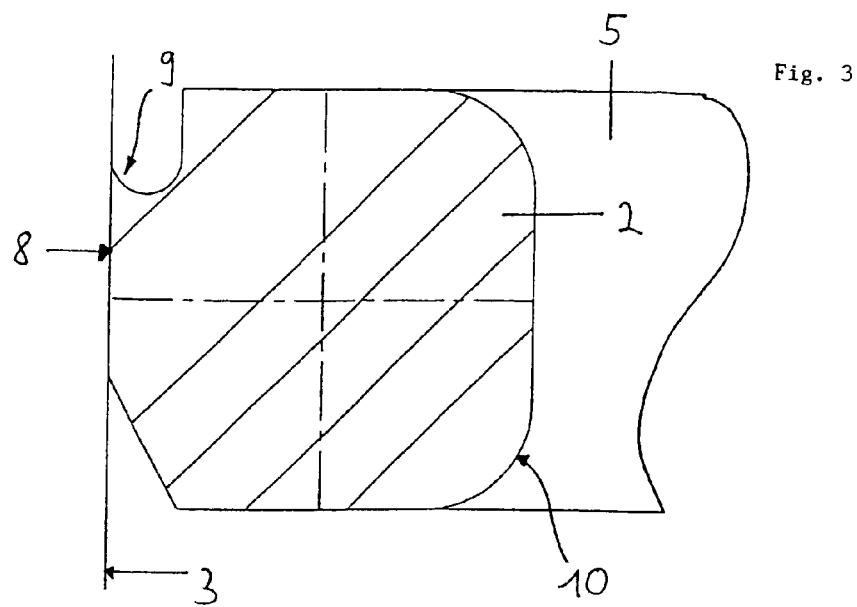
FIG. 3 depicts a representation according to FIG. 1 for a piston stopper comprising a specific sealing ring.
Figure 4:
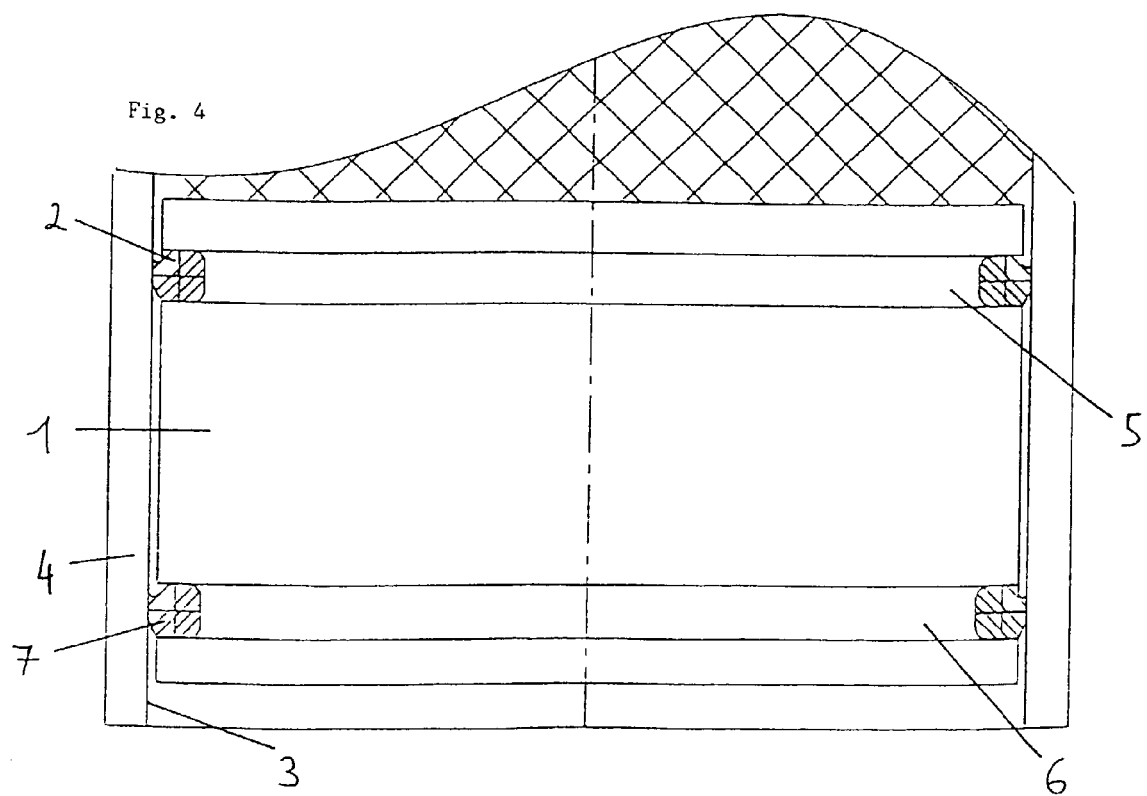
FIG. 4 depicts a representation such as in FIG. 2 for the piston stopper comprising the specific sealing ring in FIG. 3.

This latter advantage provides the option of designing the sealing ring in a specifically advantageous way in the area of its contact area with the inner wall 3 of the cylinder 4; such a preferred embodiment is shown in FIGS. 3 and 4 which correspond in their view to FIGS. 1 and 2. Except for the area of the contact area 8 between the sealing ring 2 and the inner wall 3 of the cylinder 4, this embodiment corresponds to that in FIGS. 1 and 2, and reference is made to the corresponding description.

As mentioned, the embodiment according to FIGS. 3 and 4 differs from the previous embodiment with regard to the sealing rings 2, 7 and specifically in the area of the contact area 8 between the inner wall 3 of the cylinder 4 and the sealing rings 2, 7. A concave recess is provided in this area on the front side (top in FIG. 3) of the sealing ring 2, said concave recess forming a sealing tongue 9 in the area of the wall. This sealing tongue abuts the wall 3 with its tip and when the piston stopper is advanced, diverts the liquid through the concave area towards the inner side, such that this embodiment is even better at preventing the liquid from slipping between the sealing ring 2 and the inner wall 3 when the piston stopper is advanced. This contributes towards further improving impermeability.

It may also be remarked that all the embodiments in accordance with the invention have the advantage that the stopper body 1 itself can be manufactured from a relatively hard material, such that problems arising with soft solid-rubber stoppers with formed sealing attachments, as mentioned above, do not arise, while a soft material can nonetheless be used for the sealing area.

Figure 5A:
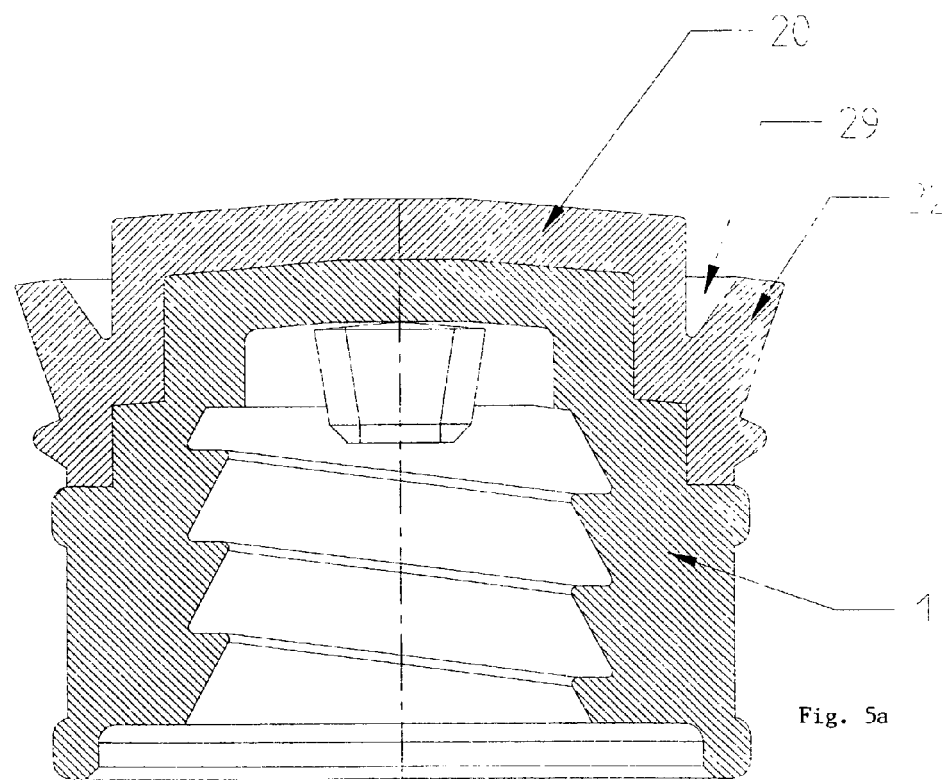
FIGS. 5a and 5b depict embodiments of a piston stopper in accordance with the invention, having a sealing cap comprising a circumferential sealing tongue.
Figure 5B:
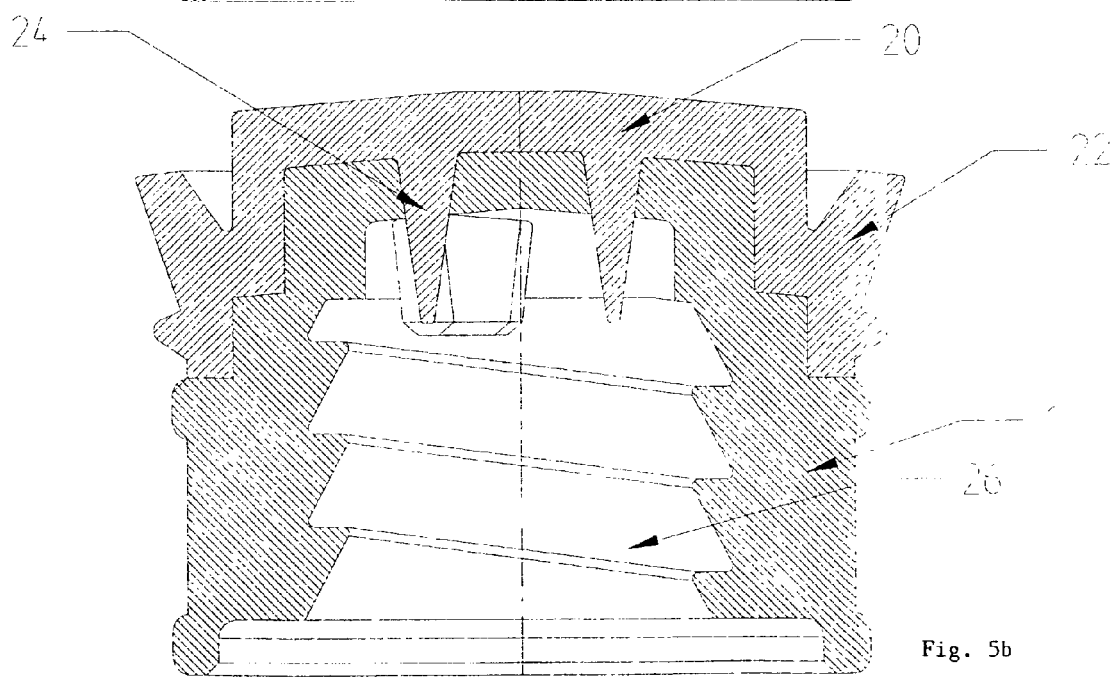

Another embodiment of a piston stopper in accordance with the invention may be understood from the sectional views shown in FIGS. 5a and 5b. The figures show angularly offset longitudinal sections through the same piston stopper, which, in accordance with this embodiment, is provided with a sealing cap 20 connected to the stopper by a material bond. The sealing cap or cap body 20 is positioned on the front end of the stopper body 1, i.e., on the side facing the volume of liquid to be displaced. A threaded mesh or connection portion 26 for receiving the plunger (not shown) of an injector is shown in the center of the stopper body in FIGS. 5a and 5b.

By being attached or positioned like a cap, the sealing cap 20 in the embodiment according to FIGS. 5a and 5b has a very large connecting area with the stopper body 1, so ensuring that the cap has an excellent hold on the stopper body 1 once the material bond connection has been established. In order to further improve this hold, the cap body 20 can also be provided with protrusions 24 extending inwards from the stopper facing side, as shown in FIG. 5b, said protrusions meshing with corresponding recesses on the front facing side of the stopper body 1. This further improves the hold or connection between the cap 20 and stopper 1, in particular when a plunger is screwed into the mesh section 26 and the tips of the protrusions 24 are then deformed flat, such that the cap is additionally attached in a positive, mechanical lock.

The cap body 20 is provided with the sealing lip 22 around its circumference, said lip projecting obliquely forward, at about the level of its base, towards the volume of liquid to be displaced. As shown in FIGS. 5a and 5b, the outer edge of this sealing lip 22 forms the radial outermost part of the piston stopper as a whole, and thus abuts the inner wall tensioned, once it has been inserted into a cylinder, ensuring an excellent seal. Just as with the proportions according to FIG. 3 and FIG. 4, the embodiment of the sealing lip 22 projecting forward generates a concave, front recess 29 which diverts the liquid through the concave area towards the inner side when the piston stopper is shifted, thus ensuring an even better seal.

Figure 8:
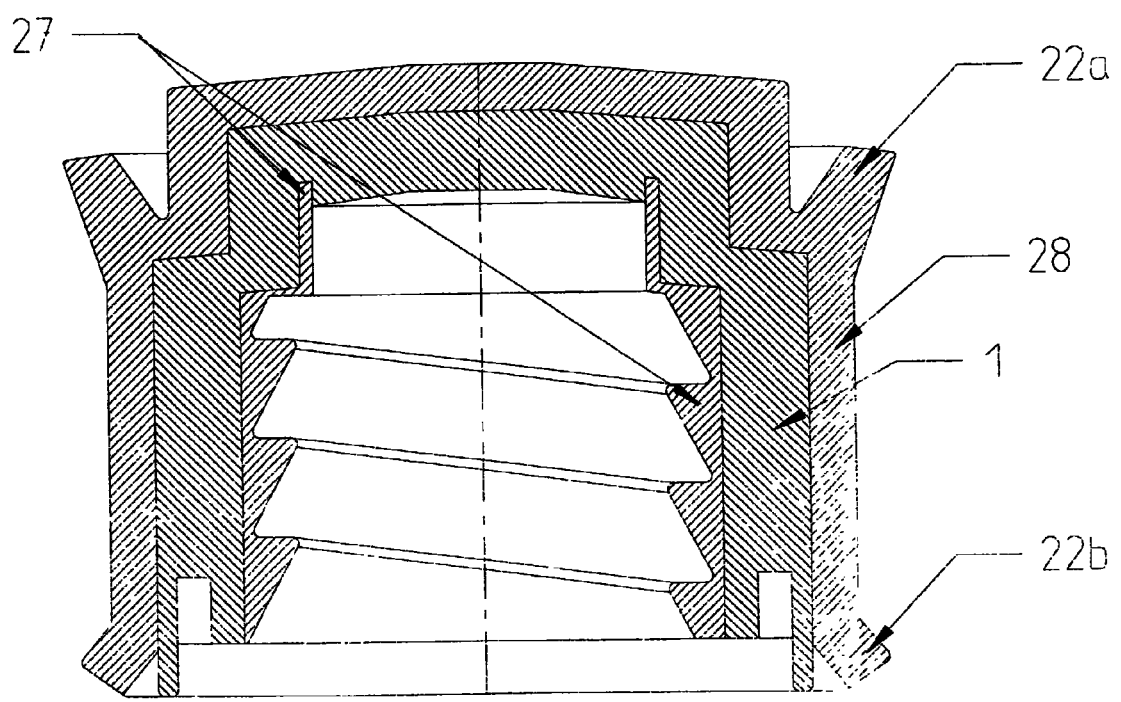
FIG. 8 depicts an embodiment of a piston stopper in accordance with the invention, comprising a threaded mesh section connected by a material bond.

FIG. 8 shows another embodiment of the present invention, in a representation which substantially corresponds to that in FIGS. 5a and 5b. On its outer side, the stopper body 1 shown here comprises a sealing cap 28 connected by a material bond, said sealing cap 28 in the present case overlapping the whole stopper body 1 to its base, thus forming two sealing lips 22a and 22b. Another aspect of the present invention becomes clear in FIG. 8, when considering the threaded mesh section or connection region for receiving a plunger, indicated here by the reference numeral 27. In the embodiment according to FIG. 8, this threaded mesh section is produced from a different, e.g., softer, material than the stopper body 1, and on its outer contact area it is connected to the stopper body 1 by a material bond. In accordance with the invention, this results in the possibility of also optimizing the piston stopper's point of mesh or connection with a component adjacent to it. The material bond of the separate or discretely provided threaded mesh section 27 can ensure that the latter accurately and precisely maintains its position, and there exists the possibility of establishing a secure and suitably damped mesh or connection with the plunger by selecting a suitable material for the mesh section.

Within the framework of the present invention, it is conceivable, in a piston stopper with conventional sealing lips, to only provide or connect the mesh section or connection region, in particular a threaded mesh section, in a material bond with the stopper body. In other words, either a seal structure or the plunger, or both, may be coupled to the stopper body in accordance with the present invention.

The present invention may be embodied in other specific forms without departing from the essential spirit or attributes thereof, and it may be used in applications outside the medical field. Described embodiments should be considered in all respects as illustrative, not restrictive.

The invention claimed is:

1. A piston stopper for an injection device for administering a medicinal substance, comprising:
    a cylindrical stopper body having a first side and a second side, the first and second sides being separated by a cylindrical wall, said first side being distal and facing the medicinal substance in the injection device, said second side being proximal and comprising a threaded section for coupling to a piston rod, and said cylindrical wall comprising one or more annular grooves; and
    at least one sealing ring arranged substantially within the one or more annular grooves, each sealing ring comprising a first contact area and a second contact area, the first contact area coupled by a material bond to one of the one or more annular grooves such that the at least one sealing ring is adhered to or integrally formed at a respective contact area in the one or more annular grooves of said stopper body, and wherein the second contact area projects substantially radially from the first contact area beyond the cylindrical body and contacts an inner wall of a cylinder of the injection device and has a substantially unvarying area, the second contact area comprising a proximal end and a distal end and a sealing tongue at the distal end, the sealing tongue contacting the inner wall of the cylinder of the injection device and being formed by a concave recess in said sealing ring, the concave recess being distally oriented, wherein, upon contact by liquid at the distal end of the sealing ring, the sealing tongue diverts liquid through the concave recess and away from the inner wall of the cylinder of the injection device.

2. The piston stopper as set forth in claim 1, wherein the sealing ring is manufactured of a softer material than the stopper body.

3. The piston stopper as set forth in claim 1, wherein said integrally formed is brought about by fusion.

4. The piston stopper as set forth in claim 1, wherein said integrally formed is brought about by bi-component injection molding.

5. The piston stopper as set forth in claim 1, wherein the stopper body is manufactured of a relatively hard, non-elastomeric thermoplast and the at least one sealing ring is manufactured of a relatively soft, elastomeric thermoplast.

6. A piston stopper for a medicine injector for delivering a medical substance, comprising:
    a cylindrical stopper body having an open end and a substantially closed end, said open end of said stopper body being threaded at an interior surface in order to couple with a piston rod having complementary threading on an exterior surface, the stopper body further comprising at least one recess; and a cylindrical sealing cap coupled to said substantially closed end of said stopper body by a material bond such that the cylindrical sealing cap is adhered to or is integrally formed at a respective contact area of said closed end of said cylindrical stopper body, the sealing cap further comprising at least one protrusion extending inwardly from a proximal side of the sealing cap for meshing with the at least one recess at the substantially closed end of the stopper body, the protrusion extending into the open end of the stopper body in an area proximal to the threaded surface and when the piston rod is screwed into the threaded interior surface, the protrusion is deformed by the piston rod such that the sealing cap is attached to the stopper body in a positive mechanical lock, said sealing cap further comprising:

a connecting wall for connecting to said closed end of said stopper body;

an annular recess encircling said connecting wall; and an annular sealing lip comprising a protrusion surrounding said annular recess, said protrusion extending obliquely forward in the direction of the closed end of said stopper body, wherein an outer edge of said protrusion forms an outermost part of the piston stopper for contacting an inner wall of a cylinder of the medicine injector.

7. The piston stopper as set forth in claim 6, further comprising another annular sealing lip formed as an annular protrusion extending obliquely forward towards the open end of said cylindrical stopper body.

8. The piston stopper as set forth in claim 6, wherein the cylindrical sealing cap is manufactured of a softer material than the cylindrical stopper body.

9. The piston stopper as set forth in claim 6, wherein said integrally formed is brought about by fusion.

10. The piston stopper as set forth in claim 6, wherein said integrally formed is brought about by bi-component injection molding.

11. The piston stopper as set forth in claim 6, wherein the cylindrical stopper body is manufactured of a relatively hard, non-elastomeric thermoplast and the cylindrical sealing cap is manufactured of a relatively soft, elastomeric thermoplast.

* * * * *